US00PP35159P3

(12) United States Plant Patent
Ruter

(10) Patent No.: US PP35,159 P3
(45) Date of Patent: May 9, 2023

(54) ***CUPRESSUS* PLANT NAMED 'RUTCUP1'**

(50) Latin Name: ***Cupressus* species**
Varietal Denomination: RutCup1

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/854,171

(22) Filed: Jun. 30, 2022

(65) Prior Publication Data

US 2023/0007819 P1 Jan. 5, 2023

Related U.S. Application Data

(60) Provisional application No. 63/216,991, filed on Jun. 30, 2021.

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
See application file for complete search history.

*Primary Examiner* — Susan McCormick Ewoldt
(74) *Attorney, Agent, or Firm* — Thomas Horstemeyer, LLP

(57) ABSTRACT

A new and distinct cultivar of *Cupressus* plant named 'RutCup1', characterized by its wider form and similar heigh and growth rate to *Cupressus arizonica* var. *glabra* cultivars; glaucous, blue-green foliage; resistance to Passalora blight; and cold hardiness to about −30° C. in laboratory tests.

2 Drawing Sheets

Figure 1:
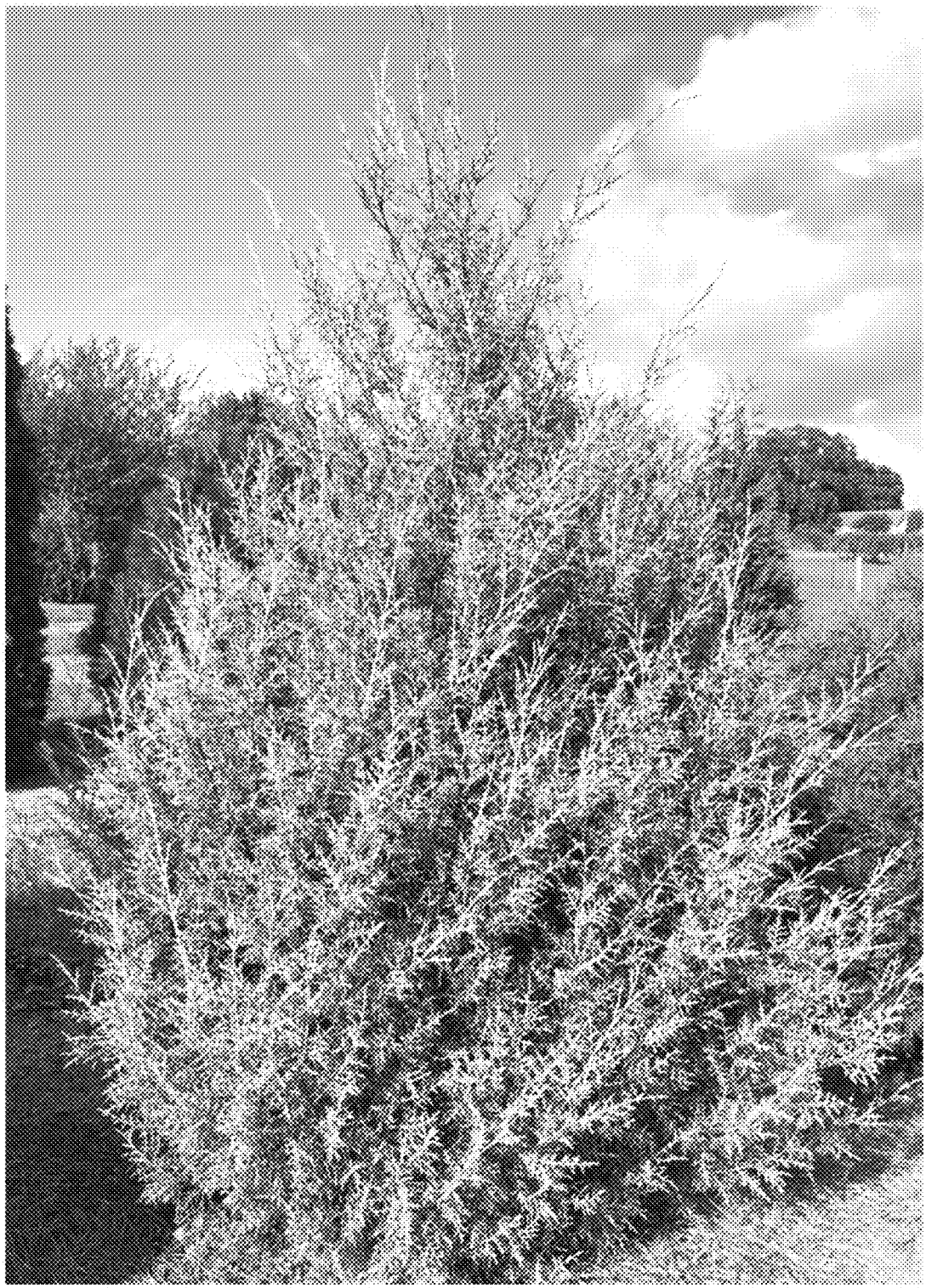

Botanical designation: *Cupressus* species.
Cultivar denomination: 'RutCup1'.

BACKGROUND OF THE INVENTION

The present invention relates to a new and distinct cultivar of *Cupressus*, botanically know as *Cupressus arizonica*, and hereinafter referred to by the cultivar name 'RutCup1'.

The new *Cupressus* 'RutCup1' is a product of open pollination of mixed *Cupressus* species in Tifton, Ga. Open-pollinated seed was collected in Tifton, Ga. in 2002 on plant labelled *C. himalaica* (not patented). Seedlings were field planted in 2005 in Dearing, Ga., and cuttings of plant I-23 (row I, plant 23) were taken in fall 2008 and field planted in Tifton in fall 2009. The new cultivar 'RutCup1' was selected for glaucous foliage and absence of Passalora blight in container and field production. The selection was tested in the lab, and 2nd year wood was found to be cold hardy down to about −30° C.

Asexual reproduction of the new *Cupressus* 'RutCup1' using hardwood terminal cuttings was first performed in Tifton, Ga. in 2008, and asexual reproduction and evaluation was subsequently also conducted in Watkinsville and Dearing, Ga. Cuttings are placed under intermittent mist with bottom heat set at about 70° F. and treated with NAA at 8000 ppm. Observations of the resulting 'RutCup1' progeny have shown that the unique features of this new *Cupressus* 'RutCup1' are stable and reproduced true to type in successive generations.

SUMMARY OF THE INVENTION

The new *Cupressus* cultivar 'RutCup1' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Cupressus* cultivar named 'RutCup1'. In combination, these traits set 'RutCup1' apart from all other existing varieties of *Cupressus* known to the inventors.

1. Attractive landscape form, wider than cultivars such as 'Blue Ice'
2. Glaucous, blue green foliage
3. Similar growth rate to other *C. arizonica* var. *glabra* cultivars
4. Resistant to Passalora blight in container and field trials; and
5. Second-year stems cold hardy (showed no damage) down to about −30° C. in laboratory tests Plants of the new *Cupressus* can be compared to the most similar cultivar *Cupressus arizonica* 'Blue Ice' (unpatented) and differ from plants of the differ from 'Blue Ice' at least in that plants of the new *Cupressus* have glaucous blue green foliage and an attractive form that is wider than 'Blue Ice' and similar cultivars. The blue green foliage color of 'RutCup1' (closest to RHS 136C) is greener than that of 'Blue Ice', which has a bluer tone (closest to RHS 133C). Female and male parent are unknown and unavailable for comparison.

BRIEF DESCRIPTION OF THE PHOTOGRAPHS

The accompanying, colored photographic illustrations show the overall appearance and distinct characteristics of the new cultivar of *Cupressus* 'RutCup1' showing the colors as true as possible. Colors in the photographs may differ slightly from the color values cited in the detailed botanical description, which accurately describes the colors of the new *Cupressus* 'RutCup1'. The photographs were taken around June, 2021 of plants grown outdoors in Watkinsville, Ga.

The photograph labeled FIG. 1 depicts a side view of a typical 5-year-old 'RutCup1' plant showing the general form and features.

Figure 2:
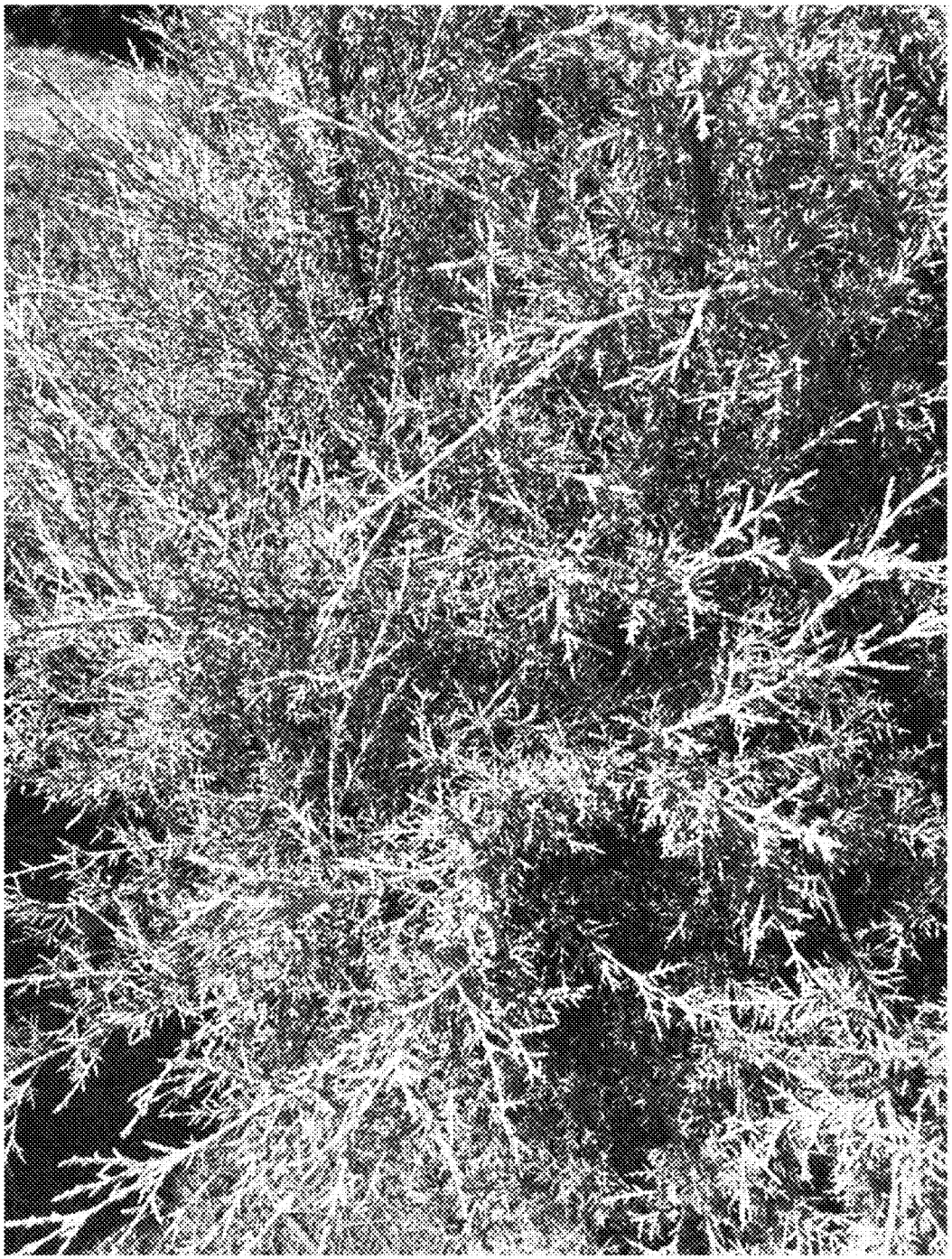

The photograph labeled FIG. 2 depicts a close-up view of the branches and needles of a typical 5-year-old 'RutCup1' plant showing the blue green foliage.

DETAILED BOTANICAL DESCRIPTION

The following traits have been consistently observed in the original plant of this new variety and in asexually propagated progeny grown in Tifton, Ga., and, to the best knowledge of the inventors, their combination forms the unique characteristics of the new variety "RutCup1'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used The aforementioned photographs and following observations, measurements, and values describe plants of the *Cupressus* cultivar named 'RutCup1'. Data were collected from a horticulture farm and nursery in Tifton, Ga. from 10-year-old plants. The average low temperatures ranged from about 20° F. to 30° F. in the winter and about 90° F. to 100° F. in summer.

Botanical classification: *Cupressus* 'RutCup1'.

Commercial classification: Ornamental conifer.

Parentage: Open pollination of mixed *Cupressus*.

Growth and propagation:

*Propagation type*.—Terminal or sub-terminal hardwood cuttings.

*Growth rate*.—Similar to *C. arizonica* var. *glabra* cultivars.

*Root description*.—Usually 1-5 roots arising from the base of the cuttings.

*Rooting habit*.—Typical for the species, not vigorous.

Plant description:

*Habit*.—Of 10-year-old plant in field — ovoid.

*Usage*.—Various uses, including landscaping, ornamental, border, hedge, and mass planting.

*Vigor*.—Moderately vigorous.

*Size of* 10 *year plant*.—A. Height: From soil level to top of plant, about 17 feet. B. Width: About 13 feet.

*Branch/stem*.—A. Quantity: About one main stems/branches per plant with numerous branches and lateral branches. B. Length: About 13 cm. C. Base Diameter: About 3.5 mm at 30 cm from tip. D. Branch angle: About 57°±2.5 from center. E: Odor (of bruised stem): Mild evergreen. F. Internode length: 22.2±1.4 mm (SD, n=10, 5 internodes per sample). G: Color (R.H.S.): year 1-3 — Greyed-orange 164A, Greyed-orange 166A, Greyed-orange 166A. H: Strength of lateral branches: Moderate. I: Pubescence: None. J: Shape: Round.

*Leaf*.—A. Leaf type: Scale-like. B. Mature size (L×W): About 1.5-3.0 mm×about 1.5-2.0 mm. C. Arrangement on stem: Decussate. D. Aspect: Closely appressed to the branchlet. E. Color (R.H.S.): Upper — Green 136C; lower — Green 136C. F. Leaf Number: Average of about 10 per cm/stem. G. Apex: Acute-acuminate. H. Base: Rounded-obtuse. I. Margin: Entire. J. Shape: Scale. K. Pubescence: None. L. Venation: None. M. Texture: Scale-like with few glands. O. Odor when crushed: Resinous.

*Long shoots*.—A. 2° branchlets/shoot: About 2.4 cm±0.3. B. 2° shoot length: About 13.5 cm±0.9. C. Color: Green 136C.

*Coning dates*.—(Data collected in 2021) (pollination) February-March.

*Pollen cone*.—A. Size (L×W): About 4 mm×2 mm. B. Color: Yellow-orange 22A to Greyed-Orange 162C. C. Stalk: Decussate about 5-9 mm. D. Shape: Ovate. E. Pollen color: Yellow-orange 16A.

*Seed cone*.—A. Size (L×W): 3 mm×2 mm. B. Color: Yellow-Green 152C to Green 133C. C. Pair of Scales: 6. D. Stalk: About 5-6 mm, curved downward.

*Seed*.—A. Size: About 4-5 mm across, with approx. 1 mm wing around the seed. B. Shape: Oval or orbicular. C. Color: Reddish-brown, not glaucous. D. Quantity: About 100 seeds/cone.

Weather/temperature tolerance: Plants of the new *Cupressus* have been observed to tolerate about −30° C. without damage in laboratory tests on two-year old wood. Hardiness USDA Zone range 6-9. Plants have not been tested north of USDA Zone 8a.

Disease/pest resistance: To date, plants of the new *Cupressus* have been observed to be resistant to Passalora blight (caused by *Passalora sequoiae*) in container and field trials.

It is claimed:

1. A new and distinct cultivar of the *Cupressus* plant named 'RutCup1' as illustrated and described herein.

* * * * *